(12) United States Patent
Cohen et al.

(10) Patent No.: US 8,383,410 B2
(45) Date of Patent: Feb. 26, 2013

(54) C4D/C4B STANDARD FOR QUANTITATIVE FLOW CYTOMETRY OF HUMORAL TRANSPLANT REJECTION

(75) Inventors: Jacques Henri Max Cohen, Reims (FR); Brigitte Reveil, Reims (FR); Aymric Kisserli, Reims (FR); Fadi Haidar, Noisy le Grand (FR); Béatrice Donvito, Reims (FR)

(73) Assignee: Universite de Reims Champagne-Ardenne, Reims Cedex (FR)

( * ) Notice: Subject to any disclaimer, the term of this patent is extended or adjusted under 35 U.S.C. 154(b) by 747 days.

(21) Appl. No.: 12/295,516

(22) PCT Filed: Mar. 30, 2007

(86) PCT No.: PCT/FR2007/000557
§ 371 (c)(1),
(2), (4) Date: May 29, 2009

(87) PCT Pub. No.: WO2007/118983
PCT Pub. Date: Oct. 25, 2007

(65) Prior Publication Data
US 2009/0305311 A1    Dec. 10, 2009

(30) Foreign Application Priority Data
Mar. 31, 2006   (FR) ...................................... 06 02834

(51) Int. Cl.
*G01N 33/53*   (2006.01)
*G01N 31/00*   (2006.01)

(52) U.S. Cl. ......... 436/15; 435/7.1; 435/7.21; 435/7.25; 435/967; 436/518; 436/520; 436/523; 436/528; 436/56; 436/63; 436/811; 436/821

(58) Field of Classification Search .................. 435/7.21, 435/7.25, 7.92, 213, 337, 372, 287.2, 967, 435/7.1; 436/507, 518, 520, 523, 528, 546, 436/548, 10, 63, 172, 811, 821, 15, 56; 422/430
See application file for complete search history.

(56) References Cited

U.S. PATENT DOCUMENTS

| 2005/0037441 A1 | 2/2005 | Ahearn et al. | |
| 2005/0042602 A1* | 2/2005 | Ahearn et al. | ..................... 435/5 |

FOREIGN PATENT DOCUMENTS

WO    WO 79/00796    * 10/1979

OTHER PUBLICATIONS

Wahrmann et al. [C4d] Flow PRA Screening—A Specific Assay for Selective Detection of Complement-Activating Anti-HLA Alloantibodies, Human Immunology 66: 526-534 (2005).*
Sim et al. (Binding of fluid-phase complement components C3 and C3b to human lymphocytes. The Biochemical Journal, 198 (3): pp. 509-518 (Sep. 15, 1981)).*
Markus Wahrmann, et al; Flow cytometry based detection of HLA alloantibody mediated classical complement activation; Journal of Immunological Methods 275 (2003) 149-160.
Markus Wahrmann, et al; [C4d] Flow PRA Screening—A Specific Assay for Selective Detection of Complement-Activating Anti-HLA Alloantibodies; Human Immunology 66, 526-534 (2005).
Peter Nickerson, et al.; C4d Deposition in Protocol Biopsies from Flow-Cytometry Crossmatch (FCXM) Positive (+ve) or (−ve) Renal Transplant Recipients Database Biosis, Accession No. PREV2002605430, Sep. 2002.
Cynthia M. Magro, et al; "Use of C4d as a Diagnostic Adjunct in Lung Allograft Biopsies"; American Journal of Transplanation 2003; 3: 1143-1154.

* cited by examiner

*Primary Examiner* — Gail R Gabel
(74) *Attorney, Agent, or Firm* — Sughrue Mion, PLLC (57) ABSTRACT

The invention concerns an internal standard used to quantitative analysis of the risk of humoral (i.e. vascular) transplant rejection. The internal standard consists of a stable composition of the C4d complement bound to a carrier consisting of erythrocytes or microparticles. The invention also concerns a method for analyzing in vitro the risk of humoral organ transplant rejection, which consists in determining the amount of component of C4d component fixed on the erythrocytes contained in a blood sample from a patient.

29 Claims, 3 Drawing Sheets

| 500 | 331 | 236 | 228 | 222 | 128.35 | 338.47 |
| 100 | 48.945 | 48.03 | 45.48 | 45.41 | 28.96 | 52.02 |
| 0 | 0 | 0 | 0 | 0 | 0 | 0 |
| | 0.674325 | 0.47140714 | 0.45608571 | 0.44327857 | 0.25435 | 0.68813571 |
| | 0.99722383 | 0.99998682 | 0.99999971 | 0.99997793 | 0.99928914 | 0.99779901 |
| | 72.5836948 | 101.866449 | 99.7180981 | 102.441225 | 113.858856 | 75.5955532 |
| | 67.4325 | 47.1407143 | 45.6085714 | 44.3278571 | 25.435 | 68.8135714 |
| | 18.4875 | 0.88928571 | 0.12857143 | 1.08214286 | 3.525 | 16.7935714 |

FIGURE 3

C4D/C4B STANDARD FOR QUANTITATIVE FLOW CYTOMETRY OF HUMORAL TRANSPLANT REJECTION

The invention relates to an internal standard for use in the quantitative analysis of the risk of humoral (i.e. vascular) transplant rejection. The internal standard is constituted by a stable composition of complement component C4d bound to a support.

The invention also relates to a method for in vitro analysis of the risk of humoral rejection of an organ transplant, in which the quantity of complement component C4d bound to erythrocytes contained in a blood sample taken from a patient is determined. Detecting the risk in question encompasses the risk of early humoral rejection or the risk of late humoral rejection, using the definitions normally employed to qualify that risk.

In particular, the present application concerns a composition for use as an internal standard for quantitative flow cytometric analysis of complement component C4d deposited on the erythrocytes of a blood sample taken from a patient.

The diagnosis of humoral rejection of an organ transplant in patients who have undergone a transplant is still frequently difficult despite the means which are now available, in particular invasive means such as biopsy of the organ in question. This difficulty may be linked to the fact that a variety of causes may be at the origin of the dysfunctions observed in the transplanted organ: infections, surgical complications, acute tubulo-interstitial functional deficiencies, recurrence of the initial disease and drug toxicity. The frequent contribution of a multitude of causes from among those which have just been cited renders the diagnosis of humoral rejection even more difficult.

With the aim of providing reliable means for diagnosis carried out on biopsies from transplanted organs, interest in the past has focused on detecting deposits of complement component C4d which have been observed to have a linear profile around peritubular capillaries in the case of acute humoral rejection, even in the absence of cellular infiltration, vascular damage or deposits of other complement fragments (Habicht, 2002). This observation was made in the case of kidney transplants (Regele H, 2002) but also in other transplanted organs (Magro, 2003, Duong Van Huyen 2004, Miller 2004).

The detection of C4d deposited in transplanted organs in the context of a diagnostic test has thus been recommended, although it appears to be difficult to read biopsies in certain complex situations, which reduces the clinical value of the observation.

On the occasion of an investigation into receptors for complement and fragments of complement present on erythrocytes from the blood of kidney transplant patients, isolated deposits of C4d were observed on the erythrocytes in various cases of acute vascular rejection and those deposits were also correlated with a C4d staining in the kidney and in certain patients presenting with histological lesions compatible with the occurrence of a humoral rejection explaining the failure of the graft. Reciprocally, no increase in the C4d deposit was observed on erythrocytes from transplanted organs which had a favorable outcome, nor in the case of acute failures of the transplant correlated with negative biopsies for the presence of C4d deposits. The same antigen was discovered in the capillaries of other transplanted organs, in particular the heart and liver, in the same situation (3, 4, 5). C4d has even been able to be detected in certain cases in the absence of conventional histological signs of rejection. Initially described in the case of early rejection, the presence of C4d has also been able to be demonstrated in the case of much later rejections, sometimes complexed with infiltrates, suggesting an associated cellular rejection. The detection of C4d on erythrocytes thus appears to be a sensitive and non-invasive test for the determination of a humoral graft rejection.

The mechanism of C4d deposition has not been completely clarified: although it is correlated with the presence of anti-HLA anti-transplant antibody in certain studies (Ionescu 2005, Weinstein 2005), activation of the direct complement pathway through antibody-dependent complement activation could not adequately explain the extra-vascular deposition of C4d or its presence on erythrocytes observed by the inventors, since the erythrocytes are free of expression of HLA.

C4, as with C3, is a molecule which is capable of binding covalently in a few seconds when it is activated. It can then degrade to the last C4d fragment, remaining locally bound via said covalent bond. In contrast to C3, for which the cell receptors for the various fractions are known, in particular CR2/CD21/C3d receptor, there is no known receptor for C4d.

The possibility of activating C4, like that of C3, without the conventional antibody pathway activation or mannose-binding lectin pathway activation has in fact been known for several decades in an area completely different from transplantation. In fact, the Chido and Rodgers blood groups are polymorphisms of C4 located on C4d and which have been described at the surface of erythrocytes before said polymorphisms are attached to the C4 plasma molecule (8, 9, 10, 11). Procedures have been developed for immunotypology allowing autologous C4 binding on erythrocytes by a relatively brief hot incubation in a medium with a low ionic strength in the presence of high concentrations of sucrose. Such procedures allow C4 and C3 to bind; they can then be reduced to C4d or C3d by digestion.

Furthermore, the isolated deposition of C4d on erythrocytes has also been observed in the case of systemic lupus erythematosus (SLE) (Manzi 2004, Liu 2005, Liu 2005), to a higher degree than in transplant patients. A "neighbour" effect, similar to the case of immune complex diseases (Freysdottir 3) has been proposed, and also a disappearance of erythrocytes carrying the complement component C3, which would result in persistence in the blood of erythrocytes having only a deposit of C4d to the exclusion of a deposit of C3. Because of the availability of C3 in plasma, the efficiency of C3 convertases (C4b2b and C3bBb) and the presence of various hydroxyl or amine acceptors on the erythrocytes to covalently bind C3, this phenomenon appears to be improbable. The C4 activation hypothesis, apart from its stabilization by C2 in normal C3 convertase as well as abnormal enzymatic cleavages resulting in it covalently binding to erythrocytes and the final degradation into C4d fragments, should also be considered (Chakravarty 1987, Atkinson 1988).

A variable but low level of C4d on erythrocytes in many healthy subjects, although it is stable in a given individual, has also been observed, suggesting a basal activation phenomenon such as that for C3 activation.

Although the mechanism for depositing C4d fragments has not been completely elucidated, the fact remains that the increase in the level of C4d observed in biopsies from transplanted organs constitutes an important indication in investigating the risk of humoral rejection.

Taking into account their observations of the presence of C4d on the surface of erythrocytes and the observation of a significantly increased presence of C4d on the surface of the erythrocytes from patients suffering from acute rejection during a multicentre kidney graft study, the inventors have defined means for detecting the risk of humoral transplant rejection, which are non-invasive and capable of providing a quantitative result based on determining complement component C4d deposited on erythrocytes in the blood of patients who have undergone a transplant.

The inventors have thus defined conditions for carrying out a quantitative assay using an internal standard, analyzed as for the sample taken from the patient. In fact, inter-trial and inter-laboratory standardization is vital to routine clinical use. It must accommodate both variations in tagging of the C4d and adjustment of the measurement apparatus when flow cytometry is used.

In other words, the means thus defined can allow detection, in a patient who has undergone an organ transplant, at different times after said transplant, of the possibility of early or late humoral rejection.

Thus, the invention provides a method for the in vitro detection of the risk of a humoral transplant rejection in a patient who has received an organ transplant, said method comprising quantitative detection of a complement component C4d, deposited on erythrocytes contained in a blood sample taken from the patient.

The method of the invention is applicable to the transplant of vascularized organs such as the heart, kidney, lung, liver, pancreas and other organs.

In a first implementation of the method of the invention, firstly, a quantitative measurement is made of the complement component C4d of the sample taken from the patient, and secondly, quantification of an internal standard, said internal standard being constituted by a composition of micro-particles or cells coated with complement component C4d. The quantity of C4d coating the micro-particles or the cells is known in terms of the signal emitted when the C4d is tagged as described in the present application.

In accordance with a particular implementation of the invention, the internal standard is constituted by cells which are erythrocytes to which the C4d fragments or molecules containing them are bound. When the following description mentions the erythrocytes of the internal standard composition, the description will alternatively apply to other cells which could replace or supplement the erythrocytes.

Detection is quantitative when the method in question can determine, directly or indirectly, the quantity of complement component C4d deposited on the erythrocytes of the blood sample which has been taken, by reference to that same C4d component measured on the internal standard.

Under the implementation conditions of the invention, the quantitative measurement, i.e. the determination of C4d by reference to an internal standard, thus allows a determination on a blood sample as to whether the observed deposit of C4d on the erythrocytes is at a normal level or, in contrast, bears witness to a humoral rejection of the graft.

The complement component C4d in the sample and in the internal standard are measured using a tag for said component, namely a molecule which has the capacity to bind specifically to the C4d component.

In a particular implementation of the invention, quantitative detection of C4d is rendered possible by tagging the molecule having a specific binding affinity for the C4d component.

Quantification results from comparing a signal emitted by the tag of the molecule having an affinity for C4d with a reference, established by means of an internal standard as described in the present application, which is analyzed under the same conditions and for the same parameter as for the blood sample which has been taken.

The complement component C4d deposited on the erythrocytes contained in a blood sample is detected and measured in the form of a C4d fragment resulting from enzymatic cleavage of complement component C4d or is detected while it is contained in another molecule, in particular in the C4b fragment. When the C4d is detected quantitatively in accordance with the invention, then it is a question of one or other of the forms provided that the binding site of C4d is accessible to the tag.

The detection method of the invention, since it is carried out on a blood sample, has the advantage of being non-invasive and of being capable of being used in the context of monitoring a transplant at various times in patients.

Further, the measurement carried out on the blood sample allows to disregard the possibility of a disease of a different nature which could affect the C4d level, since measurement of the base level before transplant may be carried out on a blood sample from the patient and then be taken into account when quantifying the complement component C4d after transplant and then be compared with the results obtained.

When the complement component C4d is bound to micro-particles, they are in particular latex micro-particles, in particular micro-spheres, of a given size and with a homogeneous composition, onto which the C4d fragments are grafted, as is or in an accessible form integrated with complement component C4b.

Examples of the micro-particles are polystyrene microspheres.

The diameter of the micro-particles, when they are microspheres, is selected to be in the range from approximately 0.1 to approximately 5 µm, for example approximately 1 to 3.5 µm, in particular 3 µm.

Grafting, onto micro-particles or onto erythrocytes, of C4d fragments or molecules containing them such as C4b fragments, may be carried out by activating the enzymatic cascade of the conventional complement pathway, or by passive adsorption. In another implementation of the invention, the graft is obtained using a chemical bond, for example a covalent bond, if necessary using an activation intermediate, for example an antibody.

When coupling is carried out with native C4d, it may be achieved by adsorption, or by covalent bonding.

When the grafted C4d is a recombinant molecule coding for all or part of C4d, since it does not include a protected thio-ester group, coupling must be carried out by artificial covalent immobilization. Any immobilization protocol may be used which can allow activation of certain functions, for example using carbodiimides, glutaraldehyde, or other types of activators for the functions of the molecule.

If necessary, spacers may also be used to distance the grafted molecule from the surface of the micro-particle or of erythrocytes. Examples of such spacers are Igs, in particular human IgGs.

In a variation, in order to graft the C4d fragments or molecules containing them onto the selected support, recourse is made to a first intermediate molecular layer between the micro-particles or the erythrocytes and said C4d fragments or molecules containing them (especially C4b), said molecular layer being chemically and/or biologically reactive, and allowing the micro-particles or erythrocytes to be functionalized so as to allow coupling to C4d fragments or to molecules containing them, for example via binding agents contained in the amine, carboxyl or hydroxyl functions of said intermediate molecules.

In yet another implementation, immobilization may be achieved using related systems of molecules allowing a non-covalent interaction between other molecules. Examples which may be cited in this respect are avidin-biotin or streptavidin-biotin systems or any related system of molecules, including systems allowing indirect immobilization via an antigen/antibody pair, to achieve immunocapture.

In a variation of the implementation of the detection method of the invention, quantification of the complement component C4d deposited on the erythrocytes of a blood sample taken from a patient is carried out firstly on a sample taken before organ transplant and secondly on a blood sample taken from the same patient after organ transplant, if appropriate at different times after said transplant to monitor the progress of the graft.

Under these conditions, quantification of complement component C4d can be carried out by subtracting the quantity of C4d (base level) present on the erythrocytes in the sample taken before transplant, from the quantity of C4d deposited on the erythrocytes measured on the blood sample taken from the same patient after organ transplant. This bound quantity of C4d is then interpolated onto the internal standard curve to convert it into a fraction of the reference standard, preferably expressed in units of that standard (arbitrary units) or in C4d antigenic sites.

In order to carry out the detection method described in the present application, a molecule is used which has a recognition and specific binding affinity for the C4d fragment, said molecule being tagged if appropriate, for example with a fluorochrome. For detection to be quantitative, the molecule having a recognition and specific binding affinity for the C4d must be used under saturation conditions or must have a single valence bond (monovalent).

The expression "specific binding" with complement component C4d means a molecule which can recognize and bind that complement component in an enhanced manner compared with any other binding with compounds of the reaction medium. Advantageously, the molecule in question has a specific binding affinity for C4d such that it does not significantly bind other components of the reaction medium.

As indicated above, the complement component C4d may be recognized as a fragment as is or may be recognized in a molecule containing it, for example in a fragment of complement component C4d.

In order to produce the micro-particles or erythrocytes coated with complement component C4d, in one particular implementation of the invention normal fresh blood or normal fresh serum is used as the source of complement. When the internal standard is constituted by erythrocytes, activation of the complement consists of auto-activation of the fresh blood used. The blood or serum is treated to allow activation of the complement in a total or partial manner in order to generate C4d fragments, and optionally, a part of them may be contained in the C4b fragment. Activation of complement to produce C4d is described in more detail in the examples below.

In a particular implementation of the invention, activation of the complement is complete, such that the micro-particles or the erythrocytes are essentially coated with C4d (with respect to C4b). In this case, the micro-particles or erythrocytes coated with C4b, C4d may optionally be treated with a proteolytic enzyme, for example trypsin or papain, in order to reduce (by degradation) the quantity of bound C4d. In this manner, and in particular if digestion is carried out with trypsin or with another proteolytic enzyme for up to 15 minutes for example, quantities of C4d are obtained on the microparticles or on the erythrocytes which are of the order of the quantities observed on the erythrocytes from blood of a patient in the event of a graft rejection.

When the support for the C4d fragments or molecules containing them is constituted by erythrocytes, these latter, once coated with C4d, are stabilized and conserved in the form of a suspension.

Stabilization is carried out using any appropriate means, for example in hypertonic sugar medium, CPD, ACD, or with para-formaldehyde or formol.

An example of a medium which can conserve the suspension of erythrocytes under appropriate stability conditions is an ID-CellStab medium (Diamed-ID, Cressier sur Morat, Switzerland) or an analogous composition medium.

The suspensions of erythrocytes or micro-particles coated with C4d may be stored at 4° C.

The quantity of C4d fragments or molecules containing them coating the micro-particles or erythrocytes is preferably of an order of magnitude close to the quantity of C4d fragments resulting from activation of complement in a pathological situation corresponding to humoral transplant rejection.

The internal standard is advantageously constituted by several populations of latex beads or of erythrocytes coated with C4d, each population having a given density of C4d which is different from that of the other populations which are used in respect of a tagging signal (for example a given level of fluorescence) in order to carry out the calibration. The various populations may result from a treatment of a first population (with a high concentration of C4d) with a proteolytic enzyme which degrades C4d.

For this reason, when the supply of C4d fragments results from complete activation of complement in a normal blood sample, it is possible to treat the particles or the erythrocytes coated with the C4d fragments to remove a portion. The treatment with an enzyme such as trypsin results, for example, in keeping the C4d fragments bound to sugars at the erythrocyte surface.

In a particular implementation of the invention, the C4d fragments deposited or accessible within the molecules containing them occupy between 100 and 5000 or even up to 10000 sites of a micro-particle or an erythrocyte of the composition constituting the internal standard.

The internal standard so prepared may also comprise other constituents, bound to the micro-particles or the erythrocytes, for example other complement components, in particular C3, without affecting the relevance of the measurement of the C4d fragments.

In the context of its use as an internal standard, the composition of micro-particles or erythrocytes is tagged with molecules having a recognition and specific binding affinity. This tagging is also carried out to analyze the micro-particles or erythrocytes of the internal standard and if appropriate to prepare calibration curves.

In a particular implementation of the invention, the molecule having a specific binding affinity for C4d (as a fragment within molecules containing it) is an antibody, for example a monoclonal antibody or a fragment of antibody having an affinity for C4d under the conditions of the present application.

In a particular implementation of the invention, monovalent fragments of antibodies are used, for example Fab fragments.

In another implementation of the invention, a natural (C4bp) or artificial C4d receptor is used.

Antibodies or fragments of antibodies which can be used to label the C4d are tagged, for example with a fluorochrome, in order to render them detectable, in particular in a flow cytometry analysis. If appropriate, said antibodies are also bound to a molecule acting as a binding intermediate with the micro-particles or erythrocytes.

Examples of appropriate antibodies for implementing the invention are biotinylated monoclonal anti-C4d antibodies from Quidel (San Diego, Calif., USA).

A particular procedure for the quantitative assay of C4 deposited as is or within molecules containing it on the surface of erythrocytes of a blood sample in accordance with the invention thus comprises a quantitative analysis using flow cytometry. In this case, the usual conditions for analysis concerning the incubation period, the quantities of sample and reagent, and the fluorescent tag are respected, as well as those for monitoring the stability of the cytometer.

Alternatively, said assay may be carried out using an ELISA test comprising a liquid phase either after lysis and dissolving the erythrocytes from a given volume of blood, or by revealing binding to the erythrocytes in the liquid phase.

Thus, the invention provides a method for the quantitative in vitro detection, by flow cytometry, of complement component C4d deposited on erythrocytes contained in a blood sample taken from a patient, comprising the following steps:

a) firstly, tagging the complement component C4d deposited on erythrocytes from said blood sample using a first molecule associated with a tag, for example a fluorescent tag, having the capacity to recognize and to specifically bind complement component C4d: and secondly, tagging one or more compositions of stabilized erythrocytes or micro-particles coated with complement component C4d using a molecule associated with a tag, for example a fluorescent tag, having the capacity to recognize and specifically bind complement component C4d, said composition or compositions constituting an internal standard for quantification;

b) introducing the sample to be quantified and the internal standard composition or compositions into a flow cytometer;

c) detecting a signal, for example fluorescence, induced by each of said specific fluorescent labels;

d) quantifying the fluorescence signal associated with the components of the C4d complement deposited on the erythrocytes of the test sample.

When several internal standard compositions are used, each corresponds to a population of micro-particles or erythrocytes coated with C4d as described in the application, with a given density of C4d which can be correlated to a given level of tagging. Each composition thus gives a standard value with which the value obtained by tagging the sample can be compared.

To determine the degree of tagging of the test sample, it is possible, for example, to position it with respect to a high internal standard and with respect to a low internal standard respectively corresponding to populations having different densities of C4d.

The sample and each internal standard composition are analyzed in the same series of measurements carried out but separately from each other since the same parameter is measured (in particular fluorescence) for each thereof.

In the context of this method, it is possible to add an optional step which consists, at the end of step d) above, in carrying out a step for comparing the value of the signal, for example the fluorescence obtained for the sample, or the number of fragments of C4d present on the erythrocytes deduced from the value of that signal, with signal values, for example, fluorescence, or with the number of C4d fragments that can be deduced therefrom, obtained on a blood sample taken before transplant or on a normal sample.

The results of the fluorescence analysis are given either in the form of a relative intensity of fluorescence corresponding to the mean or median fluorescence channel (MFC) or in the form of arbitrary units for C4d or C4d antigenic sites.

A sample/internal standard ratio may also be given.

Thus, in one implementation of the method of the invention, the fluorescence measurement is a measurement of the mean fluorescence channel for the fluorescence of each population of particles and/or erythrocytes under consideration.

The term "population" is given to categories of particles or cells more precisely micro-particles or erythrocytes, considered firstly for the test blood sample (including erythrocytes forming a first population) and secondly for compositions constituting the internal standard, coated with complement component C4d (as C4d fragment or in a molecule containing it) or stabilized erythrocytes coated with the same component and having a given density for that component.

The mean fluorescence channel measurement obtained may be corrected to subtract the background noise from the analysis, resulting in a value corresponding to the corrected mean fluorescence channel value (CMFC).

This value is expressed in arbitrary units of C4d determined on a calibration curve prepared using an internal standard which is close to the mean fluorescence channel fluorescence measurements considered above.

The measurement of C4d deposited on the erythrocytes of a blood sample from a patient associated with the same measurements carried out on an internal standard guarantees the concordance of measurements carried out on the same cytometer and the concordance of inter-laboratory measurements.

In a particular implementation of the invention, the results of the fluorescence analysis of the internal standard are expressed as the number of C4d sites on the micro-particles or on the erythrocytes. This number is obtained by applying Scatchard's method.

In this case it is possible, by referring to the internal standard, to measure the number of C4d sites on the erythrocytes of the blood sample.

The method described using the steps defined above is advantageously employed to detect the risk of humoral transplant rejection in a patient who has received an organ transplant.

It has been seen above that complement component C4d is detected using a molecule having the capacity to recognize and specifically bind said C4d, said molecule being, for example, constituted by an antibody or a fragment of antibody conjugated with a fluorescent molecule. Phycoerythrin, DTAF or other linear fluorochromes may be used.

The molecule with the capacity to recognize and specifically monovalently bind said C4d may be a monoclonal anti-C4d antibody or a fragment of said antibody.

Examples of antibody fragments which may be used in carrying out the invention are Fab fragments or sub-fragments thereof, provided that they conserve the site for recognition and binding to the C4d molecule (constituted by the C4d fragment resulting from activation of complement or by any molecule containing it, such as the C4b fragment).

The present application also concerns a stabilized suspension of erythrocytes coated with complement component C4d, said complement component C4d being bound to the erythrocytes by direct or indirect covalent bonding.

Various manners of producing erythrocytes coated with complement component C4d have been described above, in particular to obtain a covalent bond, it being understood that such functionalization of the erythrocytes must allow the bound complement component C4d access to the molecules used to detect it and quantify it.

As indicated above, the complement component C4d is not necessarily the only molecule present on the surface of the erythrocytes of the suspension. Thus, other complement components, for example C3 fragments, may also be present on the erythrocytes as long as they do not affect the quantitative measurement of the C4d component which will be measured experimentally.

The quantity of complement component C4d coating the erythrocytes of the suspension is such that it is close to the quantity normally present on the erythrocytes of a blood sample characteristic of a humoral organ transplant rejection episode.

By way of indication, the parameters affecting the quantity of C4d bound to the erythrocytes of the stabilized suspension have been given above.

The stabilized erythrocyte suspension so defined may be characterized in that it is obtained after in vitro contact of erythrocytes with a blood sample or normal fresh plasma, under controlled activation conditions (including, for example, that allowing total activation) of the complement so as to produce C4b in which C4d is accessible or C4d fragments, then recovering erythrocytes coated with complement component C4d or molecules containing it.

The C4d present on the erythrocytes of the suspension produced may be native, especially when it is obtained by activation of complement from a blood or plasma sample.

Alternatively, it may be a recombinant C4d molecule which is thereby deprived of the protected thio-ester function. In this case, the covalent bond with the erythrocytes will cause activation of the chemical functions of the molecule which may participate in covalent bonding.

The term "normal fresh blood or plasma sample" means a sample of blood or plasma taken from a patient who has not undergone organ transplant, preferably from a blood sample recovered on an anticoagulant inhibiting activation of complement, for example EDTA.

As described above, in order to produce the stabilized suspension of erythrocytes coated with complement component C4d, any known method for associating molecules with the surface of a cell may be used, and in particular covalent coupling to erythrocytes may be carried out. The coupling methods which have been described above are applicable in particular to the stabilized suspension of erythrocytes of the invention.

The invention also pertains to the use of a stabilized suspension of erythrocytes or micro-particles on which complement component C4ds have been deposited, as an internal standard in an in vitro method for detecting the risk of humoral transplant rejection in a patient.

The invention also pertains to a kit for use in the detection of the risk of humoral transplant rejection, have the following:
one or more compositions constituting an internal standard for quantifying complement component C4d, said composition or compositions comprising stabilized erythrocytes or particles in suspension, coated with complement component C4d in the form of C4d fragment or a molecule containing it;
a calibration curve for the internal standard compositions, allowing the relative fluorescence intensity measurements to be linked to arbitrary units, said curve being obtained by flow cytometry analysis, and the background noise being subtracted, if appropriate, to obtain the corrected value;
if appropriate, a composition of molecules having the capacity to recognize and bind specifically to the complement component C4d, said molecules preferably being tagged, for example with a fluorochrome.

Other characteristic properties of the invention will become apparent from the following examples and figures.

BRIEF DESCRIPTION OF THE DRAWINGS

B—Measurement of fluorescence of a population of erythrocytes coated with C4d fragments (EC4d) obtained by treating the EC4b population with trypsin, giving a mean fluorescence channel of 69.02 (including 4.97 for negative control).

In both cases, the negative control erythrocytes gave a mean fluorescence channel of 14.97.

EXAMPLES

I—Sample analysis protocol

Blood samples from patients who had undergone kidney transplant were taken from the patients on EDTA anti-coagulant on D0, D8, D30 or D90 following graft or at the time of a rejection episode.

The analyses were carried out in accordance with the ethical and legal regulations and in agreement with the Helsinki charter.

The distribution of C4d staining evaluated by flow cytometry was very broad in a given individual, many erythrocytes and little or no C4d (FIG. 1) suggesting even in certain patients a double population effect. Microscopic epi-fluorescence-based examination showed that the C4d staining on the erythrocytes was indeed very heterogeneous. This distribution was in contrast with the more homogeneous distribution of C4 on erythrocytes from patients suffering from SLE. Overall, the most manifest acute rejections showed the highest degree of C4d deposition. Quantification of C4d on erythrocytes was tested using either mean fluorescence channels (MFC) or on a flow cytometer calibrated with beads or expressing, in arbitrary units, interpolation of the MFC using an external standard produced from quantitative staining of another antigen (CR1) on the same erythrocytes revealed using the same staining system. The day-to-day reproducibility using these standardization methods was adjudged to be inadequate. Thus, it appeared to be very important to develop an internal standard, for example using stabilized erythrocytes or beads (Spycher 1991) carrying C4d in order to improve the reproducibility, which can accommodate small variations in C4d over the period during which the transplant patients are monitored and for inter-laboratory standardization allow homogeneous patient monitoring.

Methods

Blood from patients from two kidney transplant centres was collected on EDTA anti-coagulant on day D0, D8, D30 or D90 or at the time of a rejection episode. Healthy volunteers constituting negative controls were also secured.

Erythrocyte staining

After washing three times in a 0.15% PBS/BSA buffer, the erythrocytes were incubated with a biotinylated monoclonal anti-C4d antibody (Quidel San Diego, Calif., USA) for 45 minutes at 4° C. The bound antibodies were revealed with an enhanced phytoerythrin-streptavidin (Caltag Lab, Burlingham Calif., USA)/anti-streptavidin (Vector Lab, Burlingham Calif., USA) system. Flow cytometry analysis was carried out using a linear photomultiplier device to avoid any distortion of the log conversion map.

The external standard used was a CR1 antigen stained with a J3D3 biotinylated monoclonal anti-CR1 antibody and the same revealing system, then quantified using an erythrocyte reference curve having a known CR1 density (Cohen 1987). The same curve was used as an external standard to give the level of C4d on the erythrocytes in arbitrary units. The two stains were analyzed using Facstar+ or Facscan cytometers (Becton Dickinson, Mountain View, Calif., USA), calibrated using fluorescent calibration beads (Calibrite, Becton Dickinson, Mountain view, Calif., USA).

Histology

A parallel histological analysis was carried out to examine the correlation of the results obtained with those resulting from analysis of the erythrocytes. Kidney biopsies were stained with Trichome from Masson. The damage which occurred to tissues and lesions due to rejection were recorded using the BANFF system (Racusen 1999, Racusen 2003). Staining with C4d was carried out using a monoclonal anti-C4d antibody (Quidel San diego Calif., USA) and a biotinylated goat anti-mouse Ig antibody (Amersham Biosciences, Orsay, France) then an Alexa Fluor 488 streptavidin revealing system (Molecular Probes, Eugene, Oreg., USA).

Figure 1:
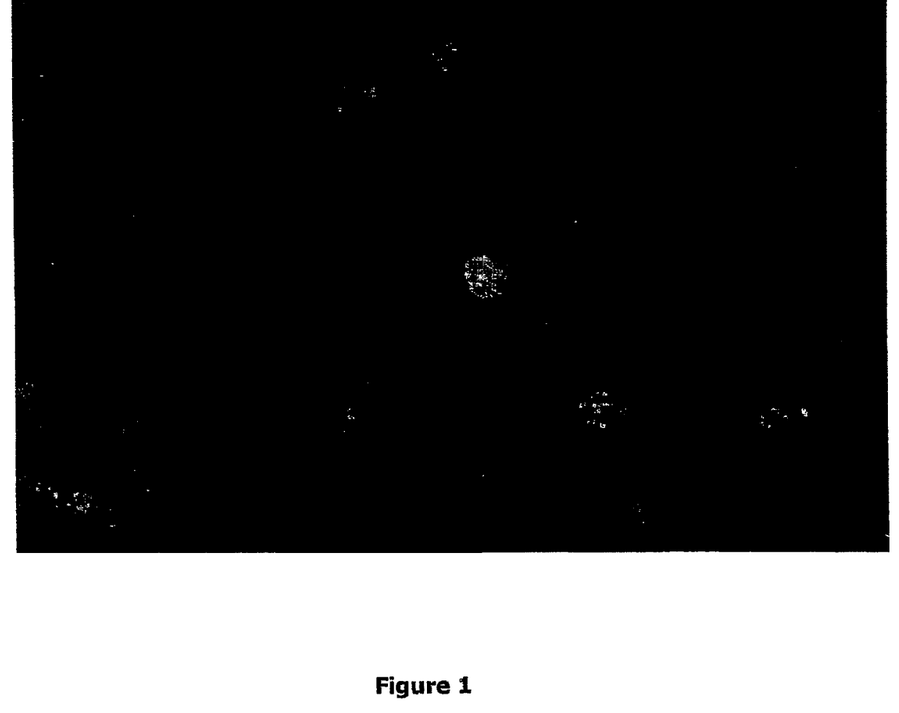
FIG. 1: sample analysis. Showing C4d deposited on erythrocytes in a blood sample.

The results of the analysis are shown in FIG. 1.

II Protocols for Preparing the Internal Standard Composition

Preparation of Latex Micro-Particles Coated With C4d

The preparation was derived from the technique described by Spycher et al (Spycher 1991).

Latex beads with a diameter of 3μ (L300 Prolab®) were incubated overnight at 4° C. with 5 mg/ml of heat aggregated IgG in a saline phosphate buffer. The heat aggregated Igs had been pre-prepared by diluting them in 10 mg/ml Tegeline® (LFB, Lille, France) in a saline phosphate buffer, and by incubating them for 30 minutes at 60° C.

Latex beads coated with Ig were coated with C4d using a conventional complement activation using a conventional route: the Ig-coated beads were exposed to fresh human serum as a source of complement, the serum being diluted to 1:20, in a veronal buffer (VBS++) with 0.15 mM Ca, 0.5 mM Mg, and 1 mM/ml BSA. Contact of the serum with the beads was maintained for 30 minutes at 37° C. Next, the beads were washed and stored at 4° C. in VBS, 5 mM EDTA, 0.2% $NaN_3$, 1 mM PMSF.

The latex beads were then stained (in the same manner as the sample erythrocytes) for quantification using a biotinylated monoclonal anti-C4d antibody (ref A704, Quidel, San Diego Calif., USA) and a phytoerythrin-streptavidin (Caltag Lab, Burlingham Calif., USA)/antistreptavidin (Vector Lab, Burlingham Calif., USA) revealing system.

The flow cytometry apparatus was adjusted so that the mean fluorescence channel (MFC) was obtained for stained beads in the channel selected as a reference for day-to-day standardization using this batch of beads.

Preparation of Erythrocytes Coated With C4d

Erythrocytes coated with C4d were prepared in vitro by means of auto-activation of autologous C4 on erythrocytes using the protocol described below:

Red Blood Cells

Human blood samples collected in vacutainers containing 0.12 ml of 0.15% EDTA were obtained from healthy volunteers who had given their informed consent in accordance with French regulations concerning the ethical aspects of medical research and also in accordance with the Helsinki charter.

Low Ionic Strength Solution (LIS)

A 10% sucrose solution containing Ca++ and Mg++ ions consisting of 100 g/l of sucrose in distilled water with 0.15 mM of Ca++ (in the form of $CaCl_2$) and 0.5 mM of Mg++ (in the form of $MgCl_2$) was used. This sucrose solution was then denoted "LIS medium".

Coating Red Blood Cells With C4b

Half of the fresh blood was added to 12.5 ml of LIS medium and mixed at 37° C. for 30 minutes. The red blood cells were washed in LIS medium by subjecting the tube to 2410 g at 4° C. for 5 minutes. This suspension of red blood cells was then denoted "EC4b". The cells were stored at 4° C. in ID-CellStab medium (Diamed-ID, Cressier sur Morat, Switzerland).

8 μl of C4b was washed in 3 ml of TBS-TBA buffer (0.12%) (Bioméerieux, Marcy L'Etoile, France-SIGMA, Lyon, France) with a view to immunostaining with anti-cd4.

Treatment With Trypsin (or Another Proteolytic Enzyme)

Treatment with a proteolytic enzyme could degrade a portion of the bound C4 to produce erythrocytes coated with different quantities of C4d.

A 30% by volume suspension of washed EC4b cells was mixed with an equal volume of trypsin-EDTA, 0.1% (Gibco, Cergy Pontoise, France) and incubated at 37° C. for 15 minutes with gentle agitation.

The erythrocytes obtained then comprised a concentration of C4d of the order of that which is encountered during humoral graft rejection, on the blood samples of a patient.

Said cells were washed in a LIS medium by subjecting the tubes to 2410 g at 4° C. for 5 minutes. This suspension of red blood cells was then denoted "EC4d". The cells were stored at 4° C. in a ID-CellStab medium (Diamed-ID, Cressier sur Morat, Switzerland).

8 μl of EC4d was washed in 3 ml of PBS/BSA buffer (0.12%) with a view to staining with an anti-C4d antibody.

The aim was to obtained densities of C4d comparable to those corresponding to the clinically observed tags and also to obtain a temporal stability sufficient to use the composition as an internal calibration standard.

Anti-cd4 Staining

Anti-C4d staining was carried out using a monoclonal anti-C4d antibody and an amplified biotinylated anti-streptavidin-Alexa 488 streptavidin system in the same manner as the staining of the patient's erythrocytes. Next, the analysis was carried out using a Becton Dickinson Facstar+flow cytometer.

Results

Figure 2A:
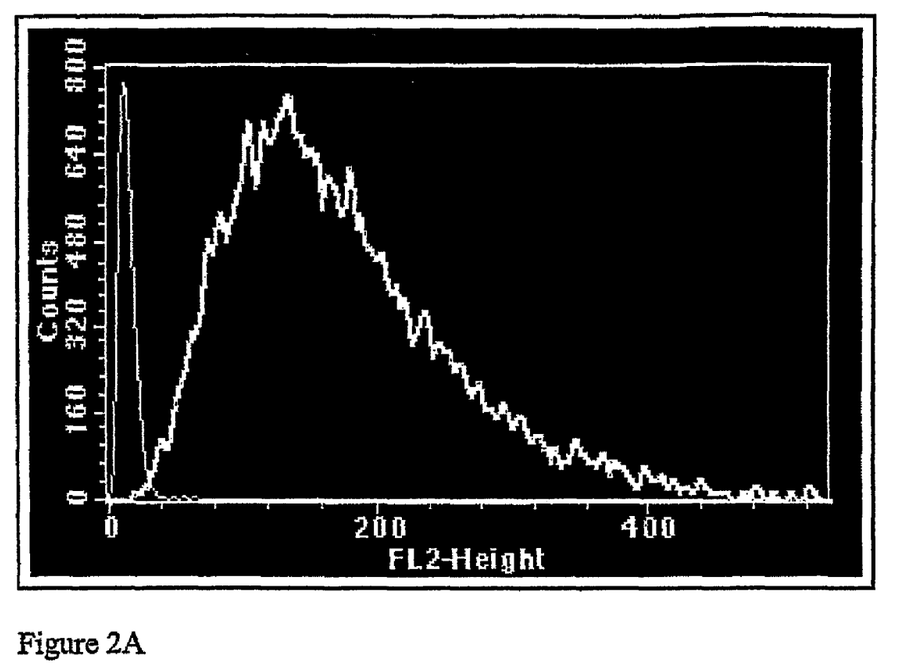
FIG. 2A—Measurement of fluorescence of a population of erythrocytes coated with C4b fragments (EC4b) in which the C4d binding site is accessible giving a mean fluorescence channel of 286.41 (including 14.97 for negative control)
Figure 2B:
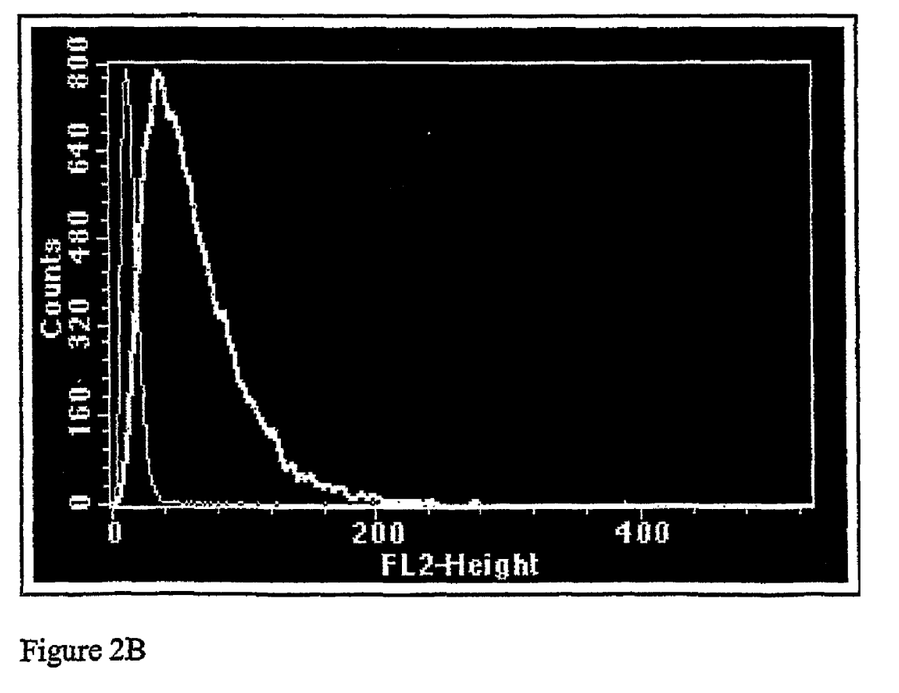

The EC4b produced a mean fluorescence channel of 271.5 while the EC4d obtained after treatment with trypsin produced a mean fluorescence channel of 57.05 and the control erythrocytes produced a mean fluorescence channel of 14.97, as can be seen in FIGS. 2A or 2B respectively.

Calibration curves (FIG. 3) were obtained with the erythrocytes coated with C4d in vitro, treated or otherwise with trypsin (which resulted in two different concentrations of C4d, which could be used to determine the C4d concentration of pathological samples). The curves were established at different times or under different conditions.

Figure 3:
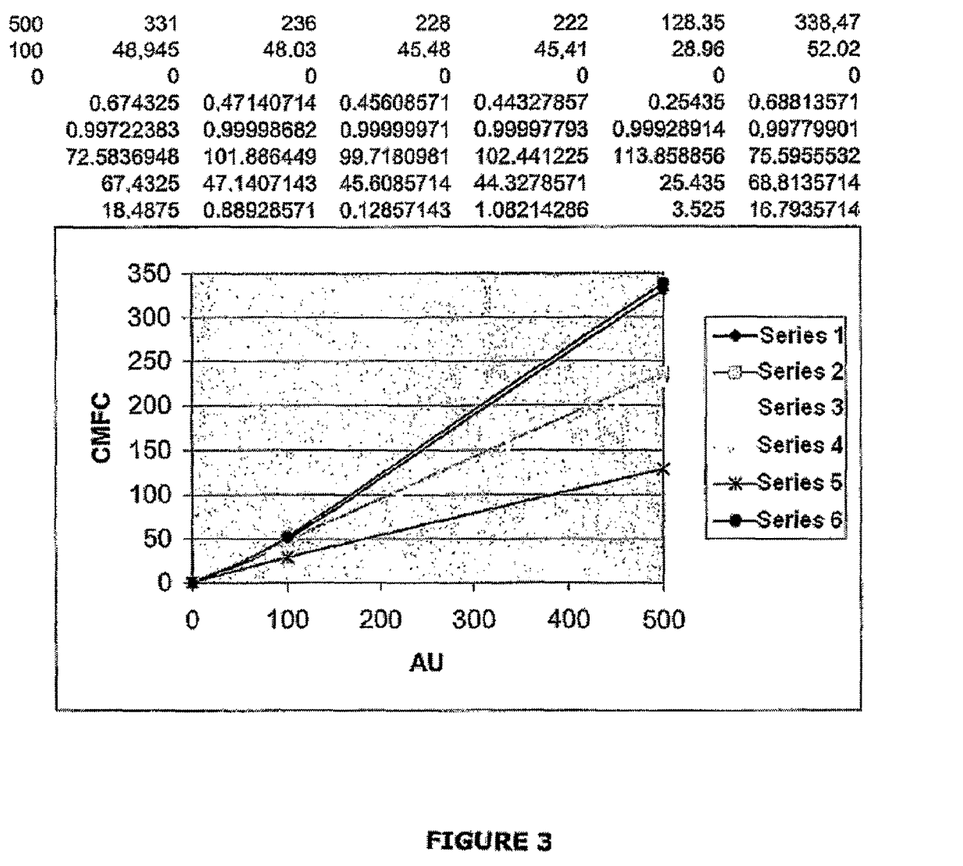
FIG. 3: Calibration curves for various populations of erythrocytes coated with C4d using the method described below.

CMFC=corrected mean fluorescence channel (minus the background noise) and AU=arbitrary units.

REFERENCES

1. Habicht, A. et al. A case of severe C4d-positive kidney allograft dysfunction in the absence of histomorphological features of rejection. Wien Klin Wochenschr. 114, 945-948 (2002).

2. Regele, H. et al. Capillary deposition of complement split product C4d in renal allografts is associated with basement membrane injury in peritubular and glomerular capillaries: a contribution of humoral immunity to chronic allograft rejection. J. Am Soc Nephrol. 13. 2371-2380 (2002).

3. Magro, C M. et al. Use of C4d as a diagnostic adjunct in lung allograft biopsies. Am J Transplant. 3, 1143-1154 (2003).

4. Duong Van Huyen, J P et al. Acute vascular humoral rejection in a sensitized cardiac graft recipient: diagnostic value of C4d immunofluorescence. Hum Pathol. 35, 385-388 (2004).

5. Miller. G. G. et al. Acute humoral rejection of human lung allografts and elevation of C4d in bronchoalveolar lavage fluid. Am J Transplant. 4. 1323-1330 (2004).

6. Ionescu, D. N. et al. C4d deposition in lung allografts is associated with circulating anti-HLA alloantibody. Transpl Immunol. 15, 63-68 (2005).

7. Weinstein, D. et al. Ultra-late antibody-mediated rejection 30 years after a living-related renal allograft. Am J Transplant. 5, 2576-2581 (2005).

8. Manzi. S. et al. Measurement of erythrocyte C4d and complement receptor 1 in systemic lupus erythemalosus. Arthritis Rheum. 50, 3596-3604 (2004).

9. Liu, C C, Manzi, S. & Ahearn, J. M. Related biomarkers for systemic lupus erythematosus: a review and perspective. Curr Opin Rheumatol. 17, 543-549 (2005).

10. Liu, C C. et al. Reticulocytes bearing C4d as biomarkers of disease activity for systemic lupus erythematosus. Arthritis Rheum. 52. 3087-3099 (2005).

11. Freysdottir, J. et al. A flow cytometric assay for measuring complement receptor 1 (CR1) and the complement fragments C3d and C4d on erythrocytes. J. Immunol Methods. 142. 45-52 (1991).

12. Chakravarti, D. N. Campbell, R. D. & Porter, R. R. The chemical structure of the C4d fragment of the human complement component C4. Mol. Immunol. 11. 1187-1197 (1987).

13. Atkinson, J P et al. Origin of the fourth component of complement related Chido and Rodgers blood group antigens. Complement. 5, 65-76 (1988).

14. Tilley, C A. Romans, D G. & Crookston. M. C. Localisation of Chido and Rodgers determinants to the C4d fragment of human C4. Nature. 276, 713-715 (1978).

15. Kerr Anderson, W. II & Stroud, R. M. Generation and enrichment of C4d in whole serum. J. Immunol Methods. 29. 323-330 (1979).

16. Yu, C Y. Bell, K T. Giles, C M., Campbell, R. D. & Porter R. R. Structural basis of the polymorphism of human complement components C4A and C4B: gene size, reactivity and antigenicity. EMBO J. 5, 2873-2881 (1986).

17. Spycher, M. O. et al. Human serum induced opsonization of immunoglobulin bi-coated polystyrene microspheres with complement components C3 and C4 as measured by flow cytometry. J. Immunol Methods. 45, 83-92 (1991).

18. Cohen. J. II et al, Enumeration of CR1 complement receptors on erythrocytes using a new method for detecting low density cell surface antigens by flow cytometry. J. Immunol. Methods. 99, 53-58 (1987).

19. Nadasdy. G. M. et al. Comparative study for the detection of peritubular capillary C4d deposition in human renal allografts using different methodologies. Hum Pathol 36, 1178-85 (2005).

20. Racusen L. C et al The Banff 97 working classification of renal allograft pathology Kidney Int. Feb: 55(2): 713-23 (1999).

21. Racusen L. C. et al Antibody-mediated rejection criteria—an addition to the Banff 97 classification of the renal allograft rejection. Am J Transplant Jun 3(6): 708-14 (2003).

The invention claimed is:

1. A method for in vitro detection of the risk of humoral transplant rejection in a patient who has received an organ transplant, said risk being linked to an increase in the presence of complement component C4d deposited on erythrocytes contained in a blood sample taken from the patient in comparison to a value obtained on the blood sample of said patient prior to transplantation or on a normal sample, comprising (i) quantitative determination of a complement component C4d deposited on erythrocytes contained in a blood sample taken from the patient, by reference to the value measured on an internal standard, wherein the internal standard consists of a support of micro-particles or stabilized erythrocytes coated with a known quantity of complement component C4d in the form of C4d fragments or molecules containing it provided that the C4d binding site is accessible for detection, the known quantity consistent with that observed on erythrocytes of transplant patients with humoral transplant rejection, (ii) comparison of the quantitative determination in step (i) with a value obtained on the blood sample of said patient prior to transplantation or on a normal sample.

2. The method according to claim 1, in which the internal standard consists of erythrocytes to which the complement component C4d is bound.

3. The method according to claim 1, in which the quantitative detection of the test sample and the internal standard employs a molecule which specifically binds to C4d.

4. The method according to claim 1, in which the detection is carried out by flow cytometry.

5. The method according to claim 1, wherein detection is carried out on the sample using enzyme-linked immunoabsorbent assay (ELISA) comprising a liquid phase.

6. The method according to claim 5 wherein the ELISA is performed in liquid phase after lysis and dissolving the erythrocytes from a given volume of blood.

7. The method according to claim 5 wherein the ELISA comprises detecting binding to the complement component C4d deposited on erythrocytes in the liquid phase.

8. The method according to claim 1, in which the complement component C4d is detected using a molecule which recognizes and specifically binds to said C4d, wherein said molecule is an antibody or a fragment of antibody conjugated with a fluorescent molecule.

9. The method according to claim 8, in which the antibody is a monoclonal anti-C4d antibody or a fragment of said antibody.

10. The detection method according to claim 1, in which the internal standard consists of a stabilized suspension of erythrocytes coated with a known quantity of complement component C4d, said complement component C4d being directly or indirectly covalently bound to the erythrocytes.

11. The method according to claim 10, wherein the method further comprises a step of in vitro detection by flow cytometry.

12. The method according to claim 10, wherein the method further comprises a step of in vitro detection by liquid phase ELISA.

13. A detection method according to claim 1, in which the internal standard consists of the stabilized suspension of erythrocytes of claim 16.

14. An internal standard which consists of a stabilized suspension of erythrocytes coated with a known quantity of complement component C4d in the form of C4d fragments or molecules containing it, provided that the C4d binding site is accessible for detection, the known quantity consistent with that observed on erythrocytes of transplant patients with humoral transplant rejection, said complement component C4d being directly or indirectly covalently bound to the erythrocytes.

15. The stabilized suspension of erythrocytes according to claim 14, wherein the quantity of C4d bound to the erythrocytes is in the range 100 to 10000 molecules of C4d.

16. The stabilized suspension of erythrocytes according to claim 14 obtained after in vitro contact of erythrocytes with a human blood sample under controlled complement activation conditions to produce C4d, then recovering erythrocytes coated with complement component C4d.

17. The stabilized suspension of erythrocytes according to claim 16, wherein after activation of the complement, the erythrocytes are treated with a composition comprising trypsin so as to essentially conserve the complement component C4d bound to sugars.

18. The stabilized suspension of erythrocytes according to claim 17, wherein the erythrocytes are coated with a known quantity of complement component C4d, said complement component C4d being directly or indirectly covalently bound to the erythrocytes, in particular in that the quantity of C4d bound to the erythrocytes is in the range 100 to 10000 molecules of C4d.

19. The stabilized suspension of erythrocytes according to one of claim 14 or 16, in which the complement component C4d is native.

20. The stabilized suspension of erythrocytes according to claim 19, in which the complement component C4d is directly or indirectly covalently coupled to erythrocytes.

21. The stabilized suspension of erythrocytes according to claim 19, in which the complement component C4d is chemically coupled to the erythrocytes.

22. The stabilized suspension of erythrocytes according to claim 19, in which the complement component C4d is coupled to the erythrocytes by means of a biological molecule.

23. The stabilized suspension of erythrocytes according to claim 14 or claim 15, in which the complement component C4d is recombinant, free of protected thio-ester function.

24. The stabilized suspension of erythrocytes according to claim 23, in which the complement component C4d is covalently coupled to erythrocytes.

25. The stabilized suspension of erythrocytes according to claim 23, in which the complement component C4d is chemically coupled to the erythrocytes.

26. The stabilized suspension of erythrocytes according to claim 23, in which the complement component C4d is coupled to the erythrocytes by means of a biological molecule.

27. A kit for use in detecting the risk of humoral transplant rejection, having the following:
- an internal standard for quantifying complement component C4d, wherein said internal standard consists of stabilized erythrocytes or microparticles in suspension, coated with a known quantity of complement component C4d in the form of C4d fragments or molecules containing it, provided that the C4d binding site is accessible for detection, the known quantity consistent with that observed on erythrocytes of transplant patients with humoral transplant rejection;
- a calibration curve for the internal standard compositions, allowing the relative fluorescence intensity measurements to be linked to units of the standard or to C4d antigenic sites, said curve being obtained by flow cytometric analysis, and the background noise being subtracted to obtain the corrected value;
- optionally, a composition of molecules having the capacity to recognize and bind specifically to complement component C4d, said molecules being tagged.

28. The kit according to claim 27, in which the stabilized erythrocytes in suspension are as defined in any one of claim 14 or 16.

29. The kit according to claim 27 wherein the molecules having the capacity to recognize and bind specifically to complement component C4d is tagged with a fluorochrome.

* * * * *